United States Patent
Kölling

(10) Patent No.: US 7,674,910 B2
(45) Date of Patent: Mar. 9, 2010

(54) PROCESS FOR PREPARING DIIMINE COMPOUNDS

(75) Inventor: Lars Kölling, Mannheim (DE)

(73) Assignee: Basell Polyolefine GmbH, Wesseling (DE)

( * ) Notice: Subject to any disclaimer, the term of this patent is extended or adjusted under 35 U.S.C. 154(b) by 310 days.

(21) Appl. No.: 11/547,900

(22) PCT Filed: Mar. 26, 2005

(86) PCT No.: PCT/EP2005/003206

§ 371 (c)(1),
(2), (4) Date: Jul. 2, 2007

(87) PCT Pub. No.: WO2005/097712

PCT Pub. Date: Oct. 20, 2005

(65) Prior Publication Data

US 2007/0282110 A1   Dec. 6, 2007

Related U.S. Application Data

(60) Provisional application No. 60/569,142, filed on May 7, 2004.

(30) Foreign Application Priority Data

Apr. 8, 2004   (DE) .................. 10 2004 018 043

(51) Int. Cl.
*C07D 213/46*   (2006.01)

(52) U.S. Cl. ..................................... 546/314

(58) Field of Classification Search ............ 546/314
See application file for complete search history.

(56) References Cited

FOREIGN PATENT DOCUMENTS

| JP | 10324689 | 12/1998 |
|----|----------|---------|
| WO | 98/27124 | 6/1998 |
| WO | 01/07491 | 2/2001 |

OTHER PUBLICATIONS

Chiericato et al, STN Accession No. 2000:322717, Doc. No. 133:111441 Abstract of Inorganica Chimica Acta (2000), 300-302, 32-42.*
Cetinkaya et al. STN Accession No. 1999:249478, Doc. No. 131:27030 Abstract of Journal of Molecular Catalysis A: Chemical (1999), 142(2), 101-112.*
C. Qian et al., :Halogen-Substituted 2,6(imino) pyridyol Iron and Cobalt Complexes Highly Active Catalysts for Polymerization and Oligomerization of Ethylene, *Organometallics*, vol. 22, p. 4312-4321 (2003).
C Qian et al., Silica-Alumina Catalyst Support, an Efficient Catalyst for Synthesis of Halolgen Substituted 2,6-Bis(imino)pyridines, *Synlett 2003*, No. 10; p. 1419-1422 (2003) (XP-002370866).
Lettau, *Chemie der Heterocyclen*, VEB, p. 17-28 (1979).

* cited by examiner

*Primary Examiner*—D. Margaret Seaman
*Assistant Examiner*—Nizal S Chandrakumar
(74) *Attorney, Agent, or Firm*—Jarrod N. Raphael

(57) ABSTRACT

Process for preparing diimine compounds, in which a dicarbonyl compound is reacted with primary amines in the presence of phosphorus pentoxide.

3 Claims, No Drawings

PROCESS FOR PREPARING DIIMINE COMPOUNDS

The present invention relates to a process for preparing diimine compounds.

The use of metallocene catalysts in the polymerization of unsaturated compounds has had a great influence on the preparation of polyolefins, since it opens up a route to new types of polyolefinic materials or to materials having improved properties. There is therefore great interest in the development of new families of catalysts for the polymerization of unsaturated compounds in order to obtain even better control over the properties of polyolefins or to obtain further novel products.

In particular, the use of transition metal catalysts comprising late transition metals is of interest because they are able to tolerate heteroatom functions. Transition metal catalysts comprising late transition metals which are suitable for the polymerization of unsaturated compounds are known from the prior art. Here, 1,2-diiminenickel and 2,6-bis(imino)pyridyliron complexes have been found to be particularly useful.

The ligand systems such as 1,2-diimine or 2,6-bis(imino) pyridyl compounds are usually prepared via condensation of the corresponding diketo compounds with primary amines. Since in this reaction two keto functions have to be converted into the corresponding imines, the yields of diimine compound are often low. Particularly when primary amines having electron-withdrawing or bulky groups are used, the yield of diimine product drops It is often the case here that only one of the two keto functions is converted into the imine. Furthermore, the reaction time usually has to be increased significantly in order to obtain at least a small yield of the diimine.

WO 98/27124 discloses the synthesis of 2,6-bis(imino) pyridyl compounds from the corresponding diketo compounds and anilines in methanol with addition of catalytic amounts of formic acid. When anilines bearing a halogen in the 2 position are used, the yield is only very low.

WO 01/07491 describes the synthesis of 2,6-bis(imino) pyridyl compounds from the corresponding keto compounds and ortho-halogen-substituted anilines in benzene in the presence of catalytic amounts of p-toluenesulfonic acid using a water separator. Here too, the yield of 2,6-bis(imino)pyridyl compound is below 50%.

In Synlett. 2003, (10), pp. 1419-1422, C. Qian et al. compares a number of synthetic routes for preparing halogen-substituted 2,6-bis(imino)pyridyl compounds. The best results are achieved by means of a combination of Al—Si-catalyst and 4Å molecular sieves.

It is an object of the present invention to provide an improved process for synthesizing diimine compounds, by means of which even primary amines having electron-withdrawing or bulky substituents can be converted into the corresponding diimine compounds in high yields.

We have accordingly found a process for preparing diimine compounds wherein a dicarbonyl compound is reacted with primary amines in the presence of phosphorus pentoxide.

In the process of the invention, a diimine compound is any compound which contains at least two imine groups —C=N— which is not part of a heteroaromatic ring.

Preference is given to diimine compounds of the formula I

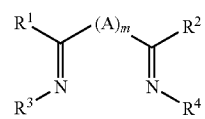

where the variables have the following meanings:

$R^1$-$R^4$ are each, independently of one another, hydrogen; $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, $NR^5_2$, or a five-, six- or seven-membered heterocycle containing at least one atom from the group consisting of N, P, O and S, where the organic radicals $R^1$-$R^4$ may also be substituted by halogens, $NR^5_2$, $OR^5$ or $SiR^6_3$ and/or two radicals $R^1$-$R^4$ may also be joined with one another or with A to form a ring, the radicals $R^5$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^6_3$, where the organic radicals $R^5$ may also be substituted by halogens and two radicals $R^5$ may also be joined to form a five- or six-membered ring, and the radicals $R^6$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^6$ may also be joined to form a five- or six-membered ring, m is 0 or 1,

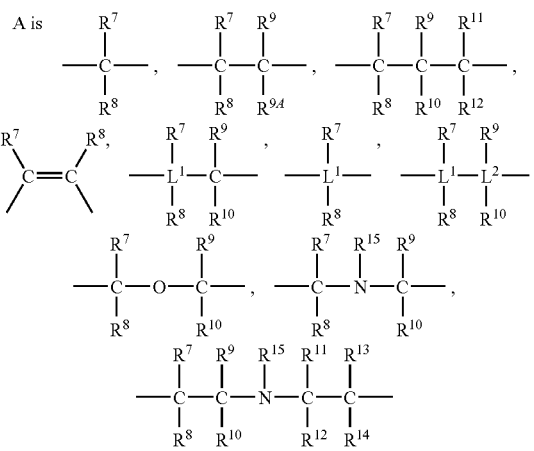

or a heteroaromatic ring system, where $L^1$-$L^2$ are each, independently of one another, silicon or germanium, $R^7$-$R^{15}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^{16}_3$, where the organic radicals $R^7$-$R^{15}$ may also be substituted by halogens and two radicals $R^7$-$R^{15}$ may also be joined to form a five- or six-membered ring, and the radicals $R^{16}$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^{16}$ may also be joined to form a five- or six-membered ring.

In the process of the invention, a dicarbonyl compound is any compound which contains at least two keto groups, —C═O, which are not part of a heteroaromatic ring, with aldehyde groups also being included.

Preference is given to dicarbonyl compounds of the formula II

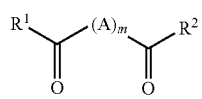

where the variables have the following meanings:

$R^1$-$R^2$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, $NR^5_2$, or a five-, six- or seven-membered heterocycle containing at least one atom from the group consisting of N, P, O and S, where the organic radicals $R^1$-$R^4$ may also be substituted by halogens, $NR^5_2$, $OR^5$ or $SiR^6_3$ and/or two radicals $R^1$-$R^2$ may also be joined with one another or with A to form a ring, the radicals $R^5$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^6_3$, where the organic radicals $R^5$ may also be substituted by halogens and two radicals $R^5$ may also be joined to form a five- or six-membered ring, and the radicals $R^6$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^6$ may also be joined to form a five- or six-membered ring, m is 0 or 1, A is

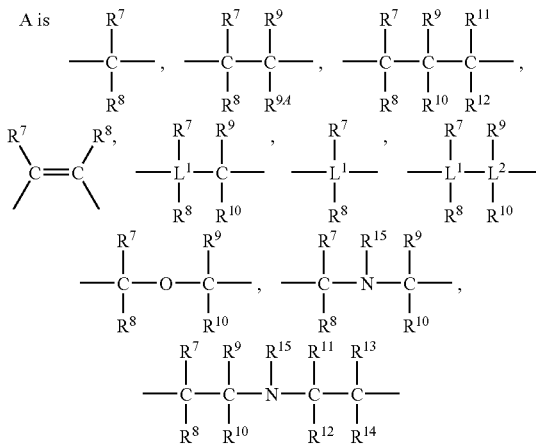

or a heteroaromatic ring system, where $L^1$-$L^2$ are each, independently of one another, silicon or germanium, $R^7$-$R^{15}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^{16}_3$, where the organic radicals $R^7$-$R^{15}$ may also be substituted by halogens and two radicals $R^7$-$R^{15}$ may also be joined to form a five- or six-membered ring, and the radicals $R^{16}$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^{16}$ may also be joined to form a five- or six-membered ring.

In the process of the invention, a primary amine is any compound which bears an $NH_2$ group, i.e. including hydrazines.

The process of the invention is preferably employed for preparing diimine compounds of the formula I by reacting the dicarbonyl compound of the formula II with primary amines in the presence of phosphorus pentoxide. Primary amines used here are $NH_2R^3$, and $NH_2R^4$, where the meanings of $R^3$ and $R^4$ and their preferred embodiments correspond to those given for the diimine compound of the formula I. Preference is given to $NH_2R^3$ and $NH_2R^4$ being identical, so that $R^3$ and $R^4$ in the diimine compound I are also identical. Examples of primary amines are methylamine, ethylamine, n-propylamine, isopropylamine, n-butylamine, tert-butylamine, sec-butylamine, isobutylamine, tert-amylamine, n-pentylamine, n-hexylamine, n-octylamine, cyclohexylamine, aniline, 2-methylaniline, 2-chloroaniline, 2-bromoaniline, 2,6-dichloroaniline, 2,4-dichloro-6-methylaniline and 2,6-dibromoaniline. $R^3$ and $R^4$ preferably contain a halogen-containing substituent.

The substituents $R^1$-$R^2$ of the diimine compound of the formula I and of the dicarbonyl compound of the formula II and $R^3$-$R^4$ of the diimine compound of the formula I can be varied within wide ranges. Possible carboorganic substituents $R^1$-$R^4$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methyiphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl, which may bear further alkyl groups as substituents, e.g. benzyl, o-, m-, p-methylbenzyl, 1- or 2-ethylphenyl, where, if appropriate, two radicals $R^1$-$R^2$ may also be joined to one another or to A to form a 5-, 6-, 7- or 8-membered ring which may also be a heterocycle containing at least one atom from the group consisting of N, P, O and S. Furthermore, $R^1$-$R^4$ can be amino $NR^5_2$, for example dimethylamino, N-pyrrolidinyl, diphenylamino or picolinyl. In this amino group, it is preferred that none of the substituents $R^5$ is hydrogen. The organic radicals $R^1$-$R^4$ may also be substituted by halogens such as fluorine, chlorine or bromine, by amino $NR^5_2$, for example dimethylamino, N-pyrrolidinyl or picolinyl, by alkoxy or aryloxy $OR^5$, e.g. methoxy, ethoxy or isopropoxy, or organosilicon substituents $SiR^6_3$, e.g. trimethylsilyl, triethylsilyl, butyldimethylsilyl, tributylsilyl, tri-tert-butylsilyl, triallylsilyl, triphenylsilyl or dimethylphenylsilyl. Possible substituents $R^5$ are the same carboorganic radicals as described in more detail above for $R^1$-$R^4$, where, if appropriate, two $R^5$ radicals may be joined to form a 5- or 6-membered ring and/or be substituted by halogen. A possible radical $R^6$ in organosilicon substituents $SiR^6{}_3$ are the same carboorganic radicals as described in more detail above for $R^1$-$R^4$, where, if appropriate, two $R^6$ radicals may also be joined to form a 5- or 6-membered ring. Preference is given to $R^3$ and $R^4$ being identical.

A is a bridge between the two keto or imino groups, preferably comprising carbon- and/or silicon- and/or n-containing bridge members. The activity of the catalyst can be influenced by a change in the length of the linkage between the imino groups.

Possible carboorganic substituents $R^7$-$R^{15}$ in the linkage A are, for example, the following: hydrogen, $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be further alkyl groups substituted by, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2,4,5-, 2,4,6- or 3,4,5-trimethylphen-1-yl, or arylalkyl, which may bear further alkyl groups as substituents, e.g. benzyl, o-, m-, p-methylbenzyl, 1- or 2-ethylphenyl, where, if appropriate, two radicals $R^7$ to $R^{15}$ may also be joined to form a 5- or 6-membered ring, cyclohexane, and the organic radicals $R^7$-$R^{15}$ may also be substituted by halogens such as fluorine, chlorine or bromine, for example pentafluorophenyl or bis-3,5-trifluoro-methylphen-1-yl. Preferred radicals $R^7$-$R^{15}$ are hydrogen, methyl, ethyl, n-propyl, isopropyl, n-butyl, isobutyl, tert-butyl, n-pentyl, n-hexyl, n-heptyl, n-octyl, benzyl, phenyl, ortho dialkyl- or dichloro-substituted phenyls, trialkyl- or trichloro-substituted phenyls, naphthyl, biphenyl and anthranyl.

Possible radicals $R^{16}$ in organosilicon substituents $SiR^{16}{}_3$ are the same radicals as described in more detail above for $R^7$-$R^{15}$, where, if appropriate, two $R^{16}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl.

A can also be a heteroaromatic ring system containing at least one atom from the group consisting of nitrogen, phosphorus, oxygen and sulfur, particularly preferably nitrogen and sulfur. Preference is given to heteroaromatics having a ring size of 5 or 6 ring atoms. Examples of 5-membered heterocycles which may contain from one to three nitrogen atoms and/or a sulfur or oxygen atom in addition to carbon atoms are 1,2-dihydrofuran, furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole or 1,2,4-triazole. Examples of 6-membered heteroaryl groups which may contain from one to four nitrogen atoms and/or a phosphorus atom are pyridine, phosphabenzene, pyridazine, pyrimidine, pyrazine, 1,3,5-triazine, 1,2,4-triazine and 1,2,3-triazine. The 5-membered and 6-membered heterocycles can also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine, dialkylamide, alkylarylamide, diarylamide, alkoxy or aryloxy or be fused with one or more aromatics or heteroaromatics. Examples of benzo-fused 5-membered heteroaryl groups are indole, indazole, benzofuran, benzothiophene, benzothiazole, benzoxazole and benzimidazole. Examples of benzo-fused 6-membered heteroaryl groups are chromane, benzopyran, quinoline, isoquinoline, cinnoline, phthalazine, quinazoline, quinoxaline, 1,10-phenanthroline and quinolizine. Nomenclature and numbering of the heterocycles has been taken from Lettau, Chemie der Heterocyclen, 1$^{st}$ edition, VEB, Weinheim 1979. The two keto or imino groups are preferably located on the heteroaromatic ring system in the ortho positions relative to the same heteroatom, preferably a nitrogen atom.

A is preferably a —$CR^7R^8$— group, substituted or unsubstituted 1,2-phenylene or —$CR^7R^8CR^9R^{10}NR^{15}CR^{11}R^{12}CR^{13}R^{14}$—. The above-described preferred embodiments of the substituents $R^7$ to $R^{15}$ are likewise preferred embodiments here. Preference is given to —$CR^7R^8$— being a —$CHR^8$—, —$CH_2$— or —$C(CH_3)_2$— group.

In a further, preferred embodiment, A has the formula III

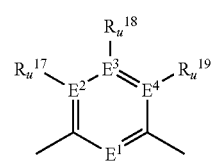

where the variables have the following meanings:

$E^1$ is nitrogen or phosphorus, in particular nitrogen, $E^2$-$E^4$ are each, independently of one another, carbon, nitrogen or phosphorus, in particular carbon, $R^{17}$-$R^{19}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, halogen, $NR^{20}{}_2$, $OR^{20}$, $SiR^{21}{}_3$, where the organic radicals $R^{17}$-$R^{19}$ may also be substituted by halogens and/or two vicinal radicals $R^{17}$-$R^{19}$ may also be joined to form a five-, six- or seven-membered ring, and/or two radicals $R^{17}$-$R^{19}$ are joined to form a five-, six- or seven-membered heterocycle containing at least one atom from the group consisting of N, P, O and S, the radicals $R^{20}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^{21}{}_3$, where the organic radicals $R^{20}$ may also be substituted by halogens and two radicals $R^{20}$ may also be joined to form a five- or six-membered ring, and the radicals $R^{21}$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^{21}$ may also be joined to form a five- or six-membered ring, u is 0 when $E^2$-$E^4$ is nitrogen or phosphorus and is 1 when $E^2$-$E^4$ is carbon.

The process of the invention has been found to be particularly useful for diimines of the formula I in which m is 0, known as 1,2-diimine systems, and those in which m is 1 and A has the formula III. The dicarbonyl compounds of the formula II from which these are prepared have the same preferred embodiments of the variables m and A.

The process of the invention is especially useful for preparing diimines of the formula IV

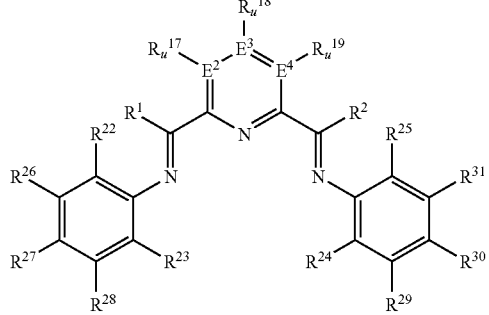

by reacting a dicarbonyl compound of the formula V

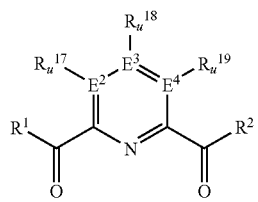

with primary amines in the presence of phosphorus pentoxide,
where the variables have the following meanings:
$E^2$-$E^4$ are each, independently of one another, carbon or nitrogen, in particular carbon,
$R^1$-$R^2$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, where the organic radicals $R^1$-$R^2$ may also be substituted by halogens, $NR^5_2$, $OR^5$ or $SiR^6_3$ and/or the radicals $R^1$-$R^2$ may also be joined to $R^{17}$-$R^{19}$ to form a ring,
$R^{17}$-$R^{19}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, halogen, $NR^{20}_2$, $OR^{20}$, $SiR^{21}_3$, where the organic radicals $R^{17}$-$R^{19}$ may also be substituted by halogens and/or two vicinal radicals $R^{17}$-$R^{19}$ may also be joined to form a five-, six- or seven-membered ring, and/or two radicals $R^{17}$-$R^{19}$ are joined to form a five-, six- or seven-membered heterocycle containing at least one atom from the group consisting of N, P, O and S,
the radicals $R^{20}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^{21}_3$, where the organic radicals $R^{20}$ may also be substituted by halogens and two radicals $R^{20}$ may also be joined to form a five- or six-membered ring, and
the radicals $R^{21}$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^{21}$ may also be joined to form a five- or six-membered ring, u is 0 when $E^2$-$E^4$ is nitrogen or phosphorus and is 1 when $E^2$-$E^4$ is carbon,
$R^{22}$-$R^{31}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, halogen, $NR^{32}_2$, $OR^{32}$, $SiR^{33}_3$, where the organic radicals $R^{22}$-$R^{31}$ may also be substituted by halogens and/or two vicinal radicals $R^{22}$-$R^{31}$ may also be joined to form a five-, six- or seven-membered ring, and/or two vicinal radicals $R^{22}$-$R^{31}$ are joined to form a five-, six- or seven-membered heterocycle containing at least one atom from the group consisting of N, P, O and S,
the radicals $R^{32}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, $SiR^{33}_3$, where the organic radicals $R^{32}$ may also be substituted by halogens or nitrogen- and oxygen-containing groups and two radicals $R^{32}$ may also be joined to form a five- or six-membered ring, and
the radicals $R^{33}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, where the organic radicals $R^{33}$ may also be substituted by halogens or nitrogen- and oxygen-containing groups and two radicals $R^{33}$ may also be joined to form a five- or six-membered ring.

The three atoms $E^2$ to $E^4$ in a molecule can be identical or different. $E^2$ to $E^4$ are each nitrogen or carbon, in particular carbon.

The substituents $R^1$-$R^2$ can be varied within wide ranges. Possible carboorganic substituents $R^{1C}$-$R^{3C}$ and $R^{8C}$-$R^{17C}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{22}$-alkenyl, which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl, which may bear further alkyl groups as substituents, e.g. benzyl, o-, m-, p-methylbenzyl, 1- or 2-ethylphenyl, where, if appropriate, a radical $R^1$ to $R^2$ may be joined to $R^{17}$-$R^{19}$ to form a 5-, 6- or 7-membered ring and/or the radicals $R^1$-$R^2$ may be joined to the radicals $R^{17}$-$R^{19}$ to form a five-, six- or seven-membered heterocycle containing at least one atom from the group consisting of N, P, O and S and/or the organic radicals $R^1$-$R^2$ may also be substituted by halogens such as fluorine, chlorine or bromine. Furthermore, $R^1$-$R^2$ may be substituted by amino $NR^5_2$, for example dimethylamino, N-pyrrolidinyl, picolinyl, by alkoxy or aryloxy $OR^5$, e.g. methoxy, ethoxy or isopropoxy, or by $SiR^6_3$, e.g. trimethylsilyl triethylsilyl, butyldimethylsilyl, tributylsilyl, tri-tert-butylsilyl, triallylsilyl, triphenylsilyl or dimethylphenylsilyl. Possible substituents $R^5$ are the same carboorganic radicals as described in more detail above for $R^1$-$R^2$, where, if appropriate, two radicals $R^5$ may be joined to form a 5- or 6-membered ring and/or be substituted by halogen. Possible radicals $R^6$ for organosilicon substituents $SiR^6_3$ are the same carboorganic radicals as described in more detail above for $R^1$-$R^2$, where, if appropriate, two radicals $R^6$ may also be joined to form a 5- or 6-membered ring.

Preferred radicals $R^1$-$R^2$ are hydrogen, methyl, ethyl, n-propyl, isopropyl, n-butyl, isobutyl, tert-butyl, n-pentyl, n-hexyl, n-heptyl, n-octyl, benzyl or phenyl.

The substituents $R^{17}$-$R^{19}$, too, can be varied within wide ranges. Possible carboorganic substituents $R^{17}$-$R^{19}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{22}$-alkenyl, which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl, which may bear further alkyl groups as substituents, e.g. benzyl, o-, m-, p-methylbenzyl, 1- or 2-ethylphenyl, here, if appropriate, two $R^{17}$ to $R^{19}$ may also be joined to form a 5-, 6- or 7-membered ring and/or two of the radicals $R^{17}$-$R^{19}$ may be joined to form a five-, six- or seven-membered heterocycle containing at least one atom from the group consisting of N, P, O and S and/or the organic radicals $R^{17}$-$R^{19}$ may also be substituted by halogens such as fluorine, chlorine or bromine. Furthermore, $R^{17}$-$R^{19}$ can be amino $NR^{20}_2$, for example dimethylamino, n-pyrrolidinyl or picolinyl, alkoxy or aryloxy $OR^{20}$, such as methoxy, ethoxy or isopropoxy or halogens such as fluorine, chlorine or bromine. Possible radicals $R^{21}$ for organosilicon substituents $SiR^{21}_3$ are the same carboorganic radicals mentioned in more detail above for $R^{17}$-$R^{19}$, where, if appropriate, two $R^{21}$ may also be joined to form a 5- or 6-membered ring, e.g. trimethylsilyl, triethylsilyl, butyldimethylsilyl, tributylsilyl, tri-tert-butylsilyl, triallylsillyl triphenylsilyl or dimethyiphenylsilyl.

Preferred radicals $R^{17}$-$R^{19}$ are hydrogen, methyl, trifluoromethyl, ethyl, n-propyl, isopropyl, n-butyl, isobutyl, tert-butyl, n-pentyl, n-hexyl, n-heptyl, n-octyl, benzyl, phenyl, fluorine, chlorine and bromine.

Possible carboorganic substituents $R^{22}$-$R^{31}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{22}$-alkenyl, which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl, which may bear further alkyl groups as substituents, e.g. benzyl, o-, m-, p-methylbenzyl, 1- or 2-ethylphenyl, here, if appropriate, two $R^{22}$ to $R^{31}$ may also be joined to form a 5-, 6- or 7-membered ring and/or two of the radicals $R^{22}$-$R^{31}$ may be joined to form a five-, six- or seven-membered heterocycle containing at least one atom from the group consisting of N, P, O and S and/or the organic radicals $R^{22}$-$R^{31}$ may also be substituted by halogens such as fluorine, chlorine or bromine. Furthermore, $R^{22}$-$R^{31}$ can be amino $NR^{32}_2$, for example dimethylamino, n-pyrrolidinyl or picolinyl, alkoxy or aryloxy $OR^{32}$, such as methoxy, ethoxy or isopropoxy or halogens such as fluorine, chlorine or bromine. Possible radicals $R^{33}$ for organosilicon substituents $SiR^{33}_3$ are the same carboorganic radicals mentioned in more detail above for $R^{22}$-$R^{31}$, where, if appropriate, two $R^{33}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. Preference is given to at least one radical $R^{22}$-$R^{31}$ being halogen such as fluorine, chlorine, bromine or iodine.

Preferred radicals $R^{22}$-$R^{31}$ are hydrogen, methyl, trifluoromethyl, ethyl, n-propyl, isopropyl, n-butyl, isobutyl, tert-butyl, n-pentyl, n-hexyl, n-heptyl, n-octyl, benzyl, phenyl, fluorine, chlorine, bromine and iodine. In particular, $R^{22}$ to $R^{25}$, $R^{27}$ and $R^{30}$ are each methyl, trifluoromethyl, ethyl, n-propyl, isopropyl, n-butyl, isobutyl, tert-butyl, n-pentyl, n-hexyl, n-heptyl, n-octyl, fluorine, chlorine or bromine and $R^{26}$, $R^{28}$, $R^{29}$ and $R^{31}$ are each hydrogen. $R^{22}$ and $R^{24}$ are particularly preferably each halogen such as fluorine, chlorine or bromine.

In particular, $R^{22}$ and $R^{24}$ are identical, $R^{23}$ and $R^{25}$ are identical, $R^{26}$ and $R^{29}$ are identical, $R^{27}$ and $R^{30}$ are identical and $R^{28}$ and $R^{31}$ are identical. This is also preferred in the preferred embodiments described further above.

Particularly preferred diimine compounds of the formula IV are 2,6-diacetylpyridinebis(2,6-dimethylphenylimine), 2,6-diacetylpyridinebis(2,4,6-trimethylphenylimine), 2,6-diacetylpyridinebis(2-chloro-6-methylphenyl), 2,6-diacetylpyridinebis(2,6-diisopropylphenylimine), 2,6-diacetylpyridinebis(2,6-dichlorophenylimine), 2,6-pyridinedicarboxaldehydebis(2,6-diisopropylphenylimine), diacetylpyridinebis(2,6-dichlorophenylimine), diacetylpyridinebis(2,6-difluorphenylimine), diacetylpyridinebis(2,6-dibromophenylimine).

Primary amines used here are

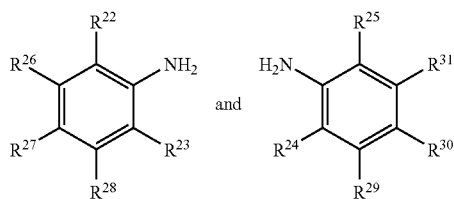

which are preferably identical. The meanings of the variables and their preferred embodiments are the same as those described above for the diimine compound IV.

The molar ratio of the dicarbonyl compound and the primary amine used is generally from 1:10 to 1:1.8, preferably from 1:5 to 1:2 and particularly preferably from 1:3 to 1:2. The order of addition of individual components is not critical. Thus, for example, the dicarbonyl compound can be initially charged and the primary amine can be added thereto.

The phosphorus pentoxide can be used as a pure substance or else as a mixture with an inert solid such as aluminum oxide, silica gel or aluminosilicate. Such mixtures are commercially available under the tradename Sicapent. The molar ratio of dicarbonyl compound to phosphorus pentoxide is preferably in the range from 1:0.1 to 1:100, preferably from 1:1 to 1:10 and particularly preferably from 1:1.5 to 1:3. The ratio of Sicapent (about 50% by weight water uptake capacity) to dicarbonyl compound is preferably in the range from 1 g of Sicapent per 0.1 mmol of dicarbonyl compound to 1 g of Sicapent per 100 mmol of dicarbonyl compound, more preferably from 1 g of Sicapent per 1 mmol of dicarbonyl compound to 1 g of Sicapent per 10 mmol of dicarbonyl compound and particularly preferably from 1 g of Sicapent per 1.8 mmol of dicarbonyl compound to 1 g of Sicapent per 6 mmol of dicarbonyl compound.

The order of addition of the phosphorus pentoxide is not critical, but it is preferably added to the mixture of dicarbonyl compound and primary amine. The total amount of phosphorus pentoxide used can be added at the beginning of the reaction, or it can be added in a number of portions during the ongoing reaction. It has been found that the process proceeds particularly quickly when the total amount of phosphorus pentoxide is added at the beginning of the reaction.

As solvents, use is usually made of anhydrous aprotic solvents such as ethers or hydrocarbons. Suitable solvents include ethers such as diethyl ether, dibutyl ether, tetrahydrofuran or ethylene glycol ethers and aromatic and aliphatic hydrocarbons such as benzene, toluene, ethylbenzene, n-pentane, n-hexane, m-hexane, isohexane, n-heptane, n-octane, and also mixtures thereof. Preference is given to using ethers and in particular tetrahydrofuran.

It has been found to be advantageous, particularly in the preparation of diimine compounds having halogen-containing substituents on the primary amine, to carry out the synthesis under a protective gas atmosphere such as nitrogen or argon.

The reaction is generally carried out at from 18 to 150° C., preferably from 30 to 110° C. and particularly preferably from 50 to 90° C. The reaction time is usually in the range from 30 minutes to 15 days, preferably from 5 hours to 5 days, particularly preferably from 8 hours to 3 days.

The work-up is carried out in a customary fashion, e.g. by removal of the solvent under reduced pressure. The product obtained can subsequently be purified by conventional methods, for example by means of chromatography of recrystallization.

The diimine compound obtained in this way can be used for the synthesis of transition metal complexes, for example iron complexes.

The process can also be used in modified form for the synthesis of diimine compounds from carbonyl-imino compounds. Since the $2^{nd}$ step in particular in the formation of the diimine compounds often gives low yields, the reaction of carbonyl-imino compound with primary imines in the presence of phosphorus pentoxide to form diimines is a further process according to the invention. The definition of the primary amines and the reaction conditions are the same as those given above. The molar ratio of the carbonyl-imino compound to the primary amine used is generally from 1:5 to 1:0.9, preferably from 1:2 to 1:1 and particularly preferably from 1:1.2 to 1:1. The molar ratio of carbonyl-imino compound to phosphorus pentoxide is preferably in the range from 1:0.1 to 1:50, preferably from 1:0.5 to 1:5 and particularly preferably from 1:1 to 1:2. The ratio of Sicapent (about 50% by weight water uptake capacity) to carbonyl-imino compound is preferably in the range from 1 g of Sicapent per 0.1 mmol of carbonyl-imino compound to 1 g of Sicapent per 50 mmol of carbonyl-imino compound, more preferably from 1 g of Sicapent per 0.5 mmol of carbonyl-imino compound to 1 g of Sicapent per 5 mmol of carbonyl-imino compound and particularly preferably from 1 g of Sicapent per 1 mmol of carbonyl-imino compound to 1 g of Sicapent per 3 mmol of carbonyl-imino compound.

In the process of the inventions, a carbonyl-imino compound is any compound which contains at least one keto group, —C=O which is not part of a heteroaromatic ring, with aldehyde groups also being included here, and which contains at least one imine group —C=N— which is not part of a heteroaromatic ring.

Preference is given to using carbonyl-imino compounds of the formula VI

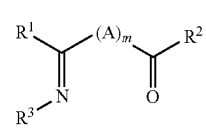

where the variables have the following meanings:

$R^1$-$R^3$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part, $NR^5_2$, or a five-, six- or seven-membered heterocycle containing at least one atom from the group consisting of N, P, O and S, where the organic radicals $R^1$-$R^4$ may also be substituted by halogens, $NR^5_2$, $OR^5$ or $SiR^6_3$ and/or two radicals $R^1$-$R^4$ may also be joined with one another or with A to form a ring, the radicals $R^5$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^6_3$, where the organic radicals $R^5$ may also be substituted by halogens and two radicals $R^5$ may also be joined to form a five- or six-membered ring, and the radicals $R^6$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^6$ may also be joined to form a five- or six-membered ring, m is 0 or 1,

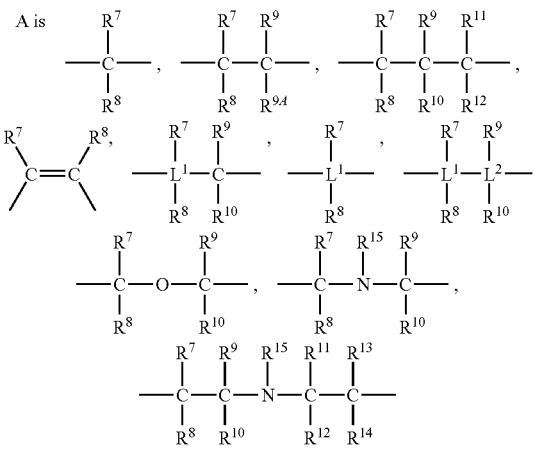

or a heteroaromatic ring system, where $L^1$-$L^2$ are each, independently of one another, silicon or germanium, $R^7$-$R^{15}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl part and 6-20 carbon atoms in the aryl part or $SiR^{16}_3$, where the organic radicals $R^7$-$R^{15}$ may also be substituted by halogens and two radicals $R^7$-$R^{15}$ may also be joined to form a five- or six-membered ring, and the radicals $R^{16}$ are each, independently of one another, hydrogen, $C_1$-$C_{22}$-alkyl, $C_2$-$C_{22}$-alkenyl, $C_6$-$C_{22}$-aryl or alkylaryl having from 1 to 10 carbon atoms in the alkyl part and 6-20 carbon atoms in the aryl part and two radicals $R^{16}$ may also be joined to form a five- or six-membered ring.

In this process, preference is likewise given to preparing diimine compounds of the formula I using primary amines $R^4NH_2$. The preferred embodiments of the variables are the same as those described above. This latter process is particularly useful for preparing diimine compounds having different radicals $R^3$ and $R^4$. The carbonyl-imino compound can be prepared by means of the customary synthetic methods, for example reaction of the dicarbonyl compound with p-toluenesulfonic acid in toluene.

The process of the invention allows, in particular, even primary amines having electron-withdrawing substituents to be converted into the corresponding diimine compounds in high yields. Furthermore, the time in which the conversion to the diimine proceeds to completion is significantly reduced.

A further advantage is that the process is also very suitable for producing commercial amounts. Amounts of 2-200 kg of the diimine compound can be prepared without problems. In contrast, when molecular sieves are used, these are often attacked during stirring and then lead to problems in the work-up.

The following experimental examples serve to illustrate the invention without implying any restriction of the scope of the invention.

EXAMPLES

Example 1

Preparation of 2,6-diacetylpyridinebis(2,4-dichloro-6-methylphenylanil)

45 g of 2,6-diacetylpyridine (0.276 mol), 106.8 g of 2,4-dichloro-6-methylaniline (0.607 mol) and 28 g of Sicapent were heated under reflux in 1200 ml of tetrahydrofuran for 7.5 hours and stirred under argon for a further 12 hours at room temperature. A further 28 g of Sicapent were added and the mixture was refluxed for another 10.5 hours and stirred for a further 13 hours at room temperature. The GC/MS indicates a yield of 86% of the product. The insoluble solid is filtered off and washed with tetrahydrofuran. The solvent was distilled off from the filtrate obtained in this way, the residue was admixed with 500 ml of methanol and subsequently stirred at 55° C. for one hour. The suspension formed in this way was filtered and the solid obtained was washed with methanol and freed of the solvent. The filtrate was freed of the solvent once again and taken up in 200 ml of methanol and admixed with a seed crystal. The product obtained in this way was filtered off and washed with methanol. This procedure was repeated on the filtrate obtained in this way. The combined product was taken up in 800 ml of methanol, stirred for one hour, filtered and the solid was washed with ether. This gave 101.8 g of 2,6-diacetylpyridinebis(2,4-dichloro-6-methylphenylanil) in a yield of 77%.

Example 2

Preparation of 2,6-diacetylpyridinebis(2,4-dichloro-6-methylphenylanil)

22.5 g of 2,6-diacetylpyridine (0.138 mol), 53.39 g of 2,4-dichloro-6-methylaniline (0.303 mol) and 64 g of Sicapent were refluxed in 500 ml of tetrahydrofuran under argon for 18 hours and the mixture was subsequently cooled to room temperature. The GC/MS indicates a yield of 91.5% of the product. The work-up was carried out as described in Example 1. This gave 2,6-diacetyl-pyridinebis(2,4-dichloro-6-methylphenylanil) in a yield of 81%.

Example 3

Preparation of 2,6-diacetylpyridinebis(2,4-dichloro-6-methylphenylanil)

4 g of 2,6-diacetylpyridine (0.025 mol), 9.49 g of 2,4-dichloro-6-methylaniline (0.054 mol) and 8.5 g of phosphorus pentoxide were refluxed in 90 ml of tetrahydrofuran for 26 hours and stirred under argon for a further 12 hours at room temperature. The GC/MS indicates a yield of 87.3% of the product. The work-up was carried out as described in Example 1. This gave 2,6-diacetylpyridinebis(2,4-dichloro-6-methylphenylanil) in a yield of 65%.

Comparative Example

Preparation of 2,6-diacetylpyridinebis(2,4-dichloro-6-methylphenylanil) by the Method of Qian et al., Organometallics 2003, 22, 4312-4321

65.6 g of 2,6-diacetylpyridine (0.4 mol), 170 g of 2,4-dichloro-6-methylaniline (0.483 mol), 32 g of Al—Si silica gel grade 135 and 160 g of molecular sieves (4 Å) were stirred in 1500 ml of toluene at 80° C. for 5 hours and a further 32 g-of silica gel grade 135 and 160 g of molecular sieves-(4 Å) were subsequently added. The mixture was stirred at 80° C. for another 8 hours (the GC/MS indicates a yield of 64% of the product), the insoluble solid was filtered off and washed twice with toluene. The solvent was distilled off from the filtrate obtained in this way, the residue was admixed with 200 ml of methanol and subsequently stirred at 55° C. for 1 hour. The suspension formed in this way was filtered and the solid obtained was washed with methanol and freed of the solvent. This gave 95 g of 2,6-diacetylpyridinebis(2,4-dichloro-6-methylphenylanil) in a yield of 47%.

The invention claimed is:

1. A process for preparing diimine compounds, which comprises reacting a dicarbonyl compound with primary amines in presence of phosphorus pentoxide, wherein the diimine compounds are of formula I,

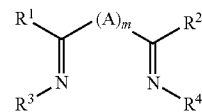

wherein:
$R^1$-$R^2$ are the same, and are selected from hydrogen, $C_1$-$C_{22}$-alkyl, $C_2$-$C_{22}$-alkenyl, $C_6$-$C_{22}$-aryl, alkylaryl comprising from 1 to 10 carbon atoms in the alkyl part and 6-20 carbon atoms in the aryl part, or a five-, six- or seven-membered heterocycle comprising at least one atom from the group consisting of N, P, O and S, wherein $R^1$-$R^2$ may be substituted by at least one halogen or $SiR^6_3$ and/or two $R^1$-$R^4$ may be joined with one another or with A to form a ring;
$R^3$-$R^4$ are the same, and are selected from hydrogen, $C_1$-$C_{22}$-alkyl, $C_2$-$C_{22}$-alkenyl, $C_6$-$C_{22}$-aryl, alkylaryl comprising from 1 to 10 carbon atoms in the alkyl part and 6-20 carbon atoms in the aryl part, or a five-, six- or seven-membered heterocycle comprising at least one atom from the group consisting of N, P, O and S, wherein $R^3$-$R^4$ may be substituted by at least one halogen or $SiR^6{}_3$ and/or two $R^1$-$R^4$ may be joined with one another or with A to form a ring;

$R^6$ are each, independently of one another, hydrogen, $C_1$-$C_{22}$-alkyl, $C_2$-$C_{22}$-alkenyl, $C_6$-$C_{22}$-aryl or alkylaryl comprising from 1 to 10 carbon atoms in the alkyl part and 6-20 carbon atoms in the aryl part, and two $R^6$ may be joined to form a five- or six-membered ring;

m is 1;

A has formula III:

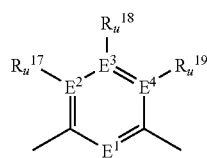

III wherein:
$E^1$ is nitrogen;
$E^2$-$E^4$ are each carbon;
$R^{17}$-$R^{19}$ are each hydrogen; and
u is 1;

and the dicarbonyl compound is of formula II,

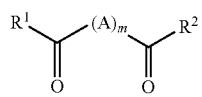

II wherein:
$R^1$-$R^2$ are the same, and are selected from hydrogen, $C_1$-$C_{22}$alkyl, $C_2$-$C_{22}$-alkenyl, $C_6$-$C_{22}$-aryl, alkylaryl comprising from 1 to 10 carbon atoms in the alkyl part and 6-20 carbon atoms in the aryl part, or a five-, six- or seven-membered heterocycle comprising at least one atom from the group consisting of N, P, O and S, wherein $R^1$-$R^2$ may be substituted by at least one halogen or $SiR^6{}_3$ and/or two $R^1$-$R^4$ may be joined with one another or with A to form a ring;

$R^6$ are each, independently of one another, hydrogen, $C_1$-$C_{22}$alkyl, $C_2$-$C_{22}$alkenyl, $C_6$-$C_{22}$-aryl or alkylaryl comprising from 1 to 10 carbon atoms in the alkyl part and 6-20 carbon atoms in the aryl part, and two $R^6$ may be joined to form a five- or six-membered ring;

m is 1; and

A has formula III:

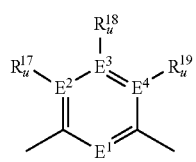

III wherein:
$E^1$ is nitrogen;
$E^2$-$E^4$ are each carbon;
$R^{17}$-$R^{19}$ are each hydrogen; and
u is 1.

2. The process according to claim 1, wherein the diimine compounds are of formula IV:

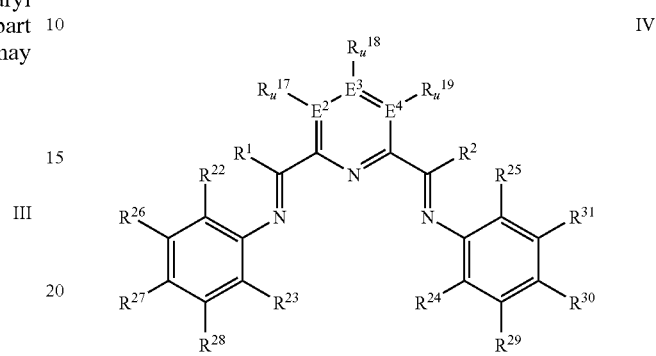

IV and are prepared by reacting a dicarbonyl compound of formula V:

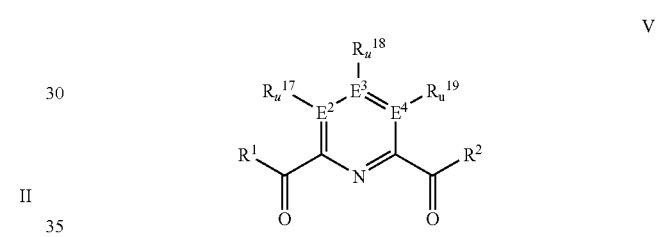

V with primary amines in presence of phosphorus pentoxide, wherein:

$E^2$-$E^4$ are each carbon;

$R^1$-$R^2$ are the same, and are selected from hydrogen, $C_1$-$C_{22}$-alkyl, $C_2$-$C_{22}$-alkenyl, $C_6$-$C_{22}$-aryl, alkylaryl comprising from 1 to 10 carbon atoms in the alkyl part and 6-20 carbon atoms in the aryl part, where $R^1$-$R^2$ may be substituted by at least one halogen, or $SiR^6{}_3$ and/or $R^1$-$R^2$ may be joined to $R^{17}$-$R^{19}$ to form a ring;

$R^{17}$-$R^{19}$ are each hydrogen, u is 1;

$R^{22}$-$R^{31}$ are each, independently of one another, hydrogen, halogen, $C_1$-$C_{22}$-alkyl, $C_2$-$C_{22}$-alkenyl, $C_6$-$C_{22}$-aryl, alkylaryl comprising from 1 to 10 carbon atoms in the alkyl part and 6-20 carbon atoms in the aryl part, $NR^{32}{}_2$, $OR^{32}$, $SiR^{33}{}_3$, where $R^{22}$-$R^{31}$ may be substituted by at least one halogen and/or two vicinal $R^{22}$-$R^{31}$ may be joined to form a five-, six- or seven-membered ring, and/or two vicinal radicals $R^{22}$-$R^{31}$ may be joined to form a five-, six- or seven-membered heterocycle comprising at least one atom from the group consisting of N, P, O and S;

$R^{32}$ are each, independently of one another, hydrogen, $C_1$-$C_{22}$-alkyl, $C_2$-$C_{22}$-alkenyl, $C_6$-$C_{22}$-aryl, alkylaryl comprising from 1 to 10 carbon atoms in the alkyl part and 6-20 carbon atoms in the aryl part, $SiR^{33}{}_3$, where $R^{32}$ may be substituted by at least one substituent selected from a halogen, a nitrogen-containing group, an oxygen-containing group, and combinations thereof, and two $R^{32}$ may be joined to form a five- or six-membered ring; and $R^{33}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, where $R^{33}$ may be substituted by at least one sustituent selected from a halogen, a nitrogen-containing group, an oxygen-containing group, and combinations thereof, and two $R^{33}$ may be joined to form a five- or six-membered ring.

3. The process according to claim 1, wherein the process is carried out in tetra-hydrofuran.

\* \* \* \* \*